United States Patent
Dziura et al.

(10) Patent No.: US 10,352,695 B2
(45) Date of Patent: Jul. 16, 2019

(54) X-RAY SCATTEROMETRY METROLOGY FOR HIGH ASPECT RATIO STRUCTURES

(71) Applicant: KLA-Tencor Corporation, Milpitas, CA (US)

(72) Inventors: Thaddeus Gerard Dziura, San Jose, CA (US); Antonio Arion Gellineau, Santa Clara, CA (US); Andrei V. Shchegrov, Campbell, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 285 days.

(21) Appl. No.: 15/230,336

(22) Filed: Aug. 5, 2016

(65) Prior Publication Data

US 2017/0167862 A1 Jun. 15, 2017

Related U.S. Application Data

(60) Provisional application No. 62/266,447, filed on Dec. 11, 2015.

(51) Int. Cl.
*G01B 15/02* (2006.01)
*G01N 23/201* (2018.01)
(Continued)

(52) U.S. Cl.
CPC ............ *G01B 15/02* (2013.01); *G01N 23/201* (2013.01); *G01N 23/2055* (2013.01); *G01B 2210/56* (2013.01)

(58) Field of Classification Search
CPC .. G01B 15/02; G01B 2210/56; G01N 23/201; G01N 23/2055
See application file for complete search history.

(56) References Cited

U.S. PATENT DOCUMENTS

| 5,608,526 A | 3/1997 | Piwonka-Corle et al. |
| 5,859,424 A | 1/1999 | Norton et al. |

(Continued)

FOREIGN PATENT DOCUMENTS

KR 10-2009-0119197 A 11/2009

OTHER PUBLICATIONS

Abe, H. et al, "Verification metrology system by using inline reference metrology," J. Micro/Nanolith. 13(4), 041405 (Oct.-Dec. 2014).

(Continued)

*Primary Examiner* — Mark R Gaworecki
(74) *Attorney, Agent, or Firm* — Spano Law Group; Joseph S. Spano

(57) ABSTRACT

Methods and systems for characterizing dimensions and material properties of high aspect ratio, vertically manufactured devices using transmission, small-angle x-ray scattering (T-SAXS) techniques are described herein. Exemplary structures include spin transfer torque random access memory (STT-RAM), vertical NAND memory (V-NAND), dynamic random access memory (DRAM), three dimensional FLASH memory (3D-FLASH), resistive random access memory (Re-RAM), and PC-RAM. In one aspect, T-SAXS measurements are performed at a number of different orientations that are more densely concentrated near the normal incidence angle and less densely concentrated at orientations that are further from the normal incidence angle. In a further aspect, T-SAXS measurement data is used to generate an image of a measured structure based on the measured intensities of the detected diffraction orders. In another further aspect, a metrology system is configured to generate models for combined x-ray and optical measurement analysis.

21 Claims, 7 Drawing Sheets

(51) Int. Cl.
*G01N 23/20* (2018.01)
*G01N 23/2055* (2018.01)

(56) References Cited

U.S. PATENT DOCUMENTS

| | | | |
|---|---|---|---|
| 6,429,943 | B1 | 8/2002 | Opsal et al. |
| 6,633,831 | B2 | 10/2003 | Nikoonahad et al. |
| 6,734,967 | B1 | 5/2004 | Piwonka-Corle et al. |
| 6,816,570 | B2 | 10/2004 | Janik et al. |
| 6,895,075 | B2 | 5/2005 | Yokhin et al. |
| 6,972,852 | B2 | 12/2005 | Opsal et al. |
| 7,478,019 | B2 | 1/2009 | Zangooie et al. |
| 7,755,764 | B2 | 7/2010 | Kwak et al. |
| 7,826,071 | B2 | 11/2010 | Shchegrov et al. |
| 7,907,264 | B1 | 3/2011 | Krishnan |
| 7,929,667 | B1 | 4/2011 | Zhuang et al. |
| 7,933,026 | B2 | 4/2011 | Opsal et al. |
| 8,860,937 | B1 | 10/2014 | Dziura et al. |
| 9,915,522 | B1 | 3/2018 | Jiang |
| 2006/0115047 | A1 | 6/2006 | Yokhin |
| 2013/0114085 | A1 | 5/2013 | Wang et al. |
| 2013/0304424 | A1 | 11/2013 | Bakeman et al. |
| 2014/0019097 | A1 | 1/2014 | Bakeman et al. |
| 2014/0111791 | A1 | 4/2014 | Manassen et al. |
| 2014/0172394 | A1 | 6/2014 | Kuznetsov et al. |
| 2014/0222380 | A1 | 8/2014 | Kuznetsov et al. |
| 2014/0297211 | A1 | 10/2014 | Pandev et al. |
| 2014/0316730 | A1 | 10/2014 | Shchegrov et al. |
| 2015/0042984 | A1 | 2/2015 | Pandev et al. |
| 2015/0046118 | A1 | 2/2015 | Pandev et al. |
| 2015/0051877 | A1* | 2/2015 | Bakeman ............ G01N 23/223 703/1 |
| 2015/0110249 | A1 | 4/2015 | Bakeman et al. |
| 2015/0117610 | A1 | 4/2015 | Veldman et al. |
| 2015/0146841 | A1 | 5/2015 | Lin et al. |
| 2015/0204664 | A1 | 7/2015 | Bringoltz et al. |
| 2015/0300965 | A1 | 10/2015 | Sezginer et al. |

OTHER PUBLICATIONS

International Search Report dated Jan. 11, 2017, for PCT Application No. PCT/US2016/054758 filed Sep. 30, 2016 by KLA-Tencor Corporation, 3 pages.

* cited by examiner

X-RAY SCATTEROMETRY METROLOGY FOR HIGH ASPECT RATIO STRUCTURES

CROSS REFERENCE TO RELATED APPLICATION

The present application for patent claims priority under 35 U.S.C. § 119 from U.S. provisional patent application Ser. No. 62/266,447, entitled "X-ray Scattering for Vertically Manufactured Devices," filed Dec. 11, 2015, the subject matter of which is incorporated herein by reference in its entirety.

TECHNICAL FIELD

The described embodiments relate to metrology systems and methods, and more particularly to methods and systems for improved measurement accuracy.

BACKGROUND INFORMATION

Semiconductor devices such as logic and memory devices are typically fabricated by a sequence of processing steps applied to a specimen. The various features and multiple structural levels of the semiconductor devices are formed by these processing steps. For example, lithography among others is one semiconductor fabrication process that involves generating a pattern on a semiconductor wafer. Additional examples of semiconductor fabrication processes include, but are not limited to, chemical-mechanical polishing, etch, deposition, and ion implantation. Multiple semiconductor devices may be fabricated on a single semiconductor wafer and then separated into individual semiconductor devices.

Metrology processes are used at various steps during a semiconductor manufacturing process to detect defects on wafers to promote higher yield. A number of metrology based techniques including scatterometry and reflectometry implementations and associated analysis algorithms are commonly used to characterize critical dimensions, film thicknesses, composition and other parameters of nanoscale structures.

Traditionally, scatterometry critical dimension (SCR) measurements are performed on targets consisting of thin films and/or repeated periodic structures. During device fabrication, these films and periodic structures typically represent the actual device geometry and material structure or an intermediate design. As devices (e.g., logic and memory devices) move toward smaller nanometer-scale dimensions, characterization becomes more difficult. Devices incorporating complex three-dimensional geometry and materials with diverse physical properties contribute to characterization difficulty. For example, modern memory structures are often high-aspect ratio, three-dimensional structures that make it difficult for optical radiation to penetrate to the bottom layers. Optical metrology tools utilizing infrared to visible light can penetrate many layers of translucent materials, but longer wavelengths that provide good depth of penetration do not provide sufficient sensitivity to small anomalies. In addition, the increasing number of parameters required to characterize complex structures (e.g., FinFETs), leads to increasing parameter correlation. As a result, the parameters characterizing the target often cannot be reliably decoupled with available measurements.

In one example, longer wavelengths (e.g. near infrared) have been employed in an attempt to overcome penetration issues for 3D FLASH devices that utilize polysilicon as one of the alternating materials in the stack. However, the mirror like structure of 3D FLASH intrinsically causes decreasing light intensity as the illumination propagates deeper into the film stack. This causes sensitivity loss and correlation issues at depth. In this scenario, SCD is only able to successfully extract a reduced set of metrology dimensions with high sensitivity and low correlation.

In another example, opaque, high-k materials are increasingly employed in modern semiconductor structures. Optical radiation is often unable to penetrate layers constructed of these materials. As a result, measurements with thin-film scatterometry tools such as ellipsometers or reflectometers are becoming increasingly challenging.

In response to these challenges, more complex optical metrology tools have been developed. For example, tools with multiple angles of illumination, shorter illumination wavelengths, broader ranges of illumination wavelengths, and more complete information acquisition from reflected signals (e.g., measuring multiple Mueller matrix elements in addition to the more conventional reflectivity or ellipsometric signals) have been developed. However, these approaches have not reliably overcome fundamental challenges associated with measurement of many advanced targets (e.g., complex 3D structures, structures smaller than 10 nm, structures employing opaque materials) and measurement applications (e.g., line edge roughness and line width roughness measurements).

Atomic force microscopes (AFM) and scanning-tunneling microscopes (STM) are able to achieve atomic resolution, but they can only probe the surface of the specimen. In addition, AFM and STM microscopes require long scanning times. Scanning electron microscopes (SEM) achieve intermediate resolution levels, but are unable to penetrate structures to sufficient depth. Thus, high-aspect ratio holes are not characterized well. In addition, the required charging of the specimen has an adverse effect on imaging performance. X-ray reflectometers also suffer from penetration issues that limit their effectiveness when measuring high aspect ratio structures.

To overcome penetration depth issues, traditional imaging techniques such as TEM, SEM etc., are employed with destructive sample preparation techniques such as focused ion beam (FIB) machining, ion milling, blanket or selective etching, etc. For example, transmission electron microscopes (TEM) achieve high resolution levels and are able to probe arbitrary depths, but TEM requires destructive sectioning of the specimen. Several iterations of material removal and measurement generally provide the information required to measure the critical metrology parameters throughout a three dimensional structure. But, these techniques require sample destruction and lengthy process times. The complexity and time to complete these types of measurements introduces large inaccuracies due to drift of etching and metrology steps. In addition, these techniques require numerous iterations which introduce registration errors.

To further improve device performance, the semiconductor industry continues to focus on vertical integration, rather than lateral scaling. Thus, accurate measurement of complex, fully three dimensional structures is crucial to ensure viability and continued scaling improvements. Future metrology applications present challenges for metrology due to increasingly small resolution requirements, multi-parameter correlation, increasingly complex geometric structures including high aspect ratio structures, and increasing use of opaque materials. Thus, methods and systems for improved CD measurements are desired.

SUMMARY

Methods and systems for characterizing dimensions and material properties of high aspect ratio, vertically manufactured devices using transmission, small-angle x-ray scattering (T-SAXS) techniques are described herein. In some examples, T-SAXS is employed to measure critical dimensions, thicknesses, overlay, and material properties of high aspect ratio semiconductor structures including, but not limited to, spin transfer torque random access memory (STT-RAM), vertical NAND memory (V-NAND), dynamic random access memory (DRAM), three dimensional FLASH memory (3D-FLASH), resistive random access memory (Re-RAM), and PC-RAM.

A T-SAXS measurement involves illuminating a sample with an X-ray beam at one or more orientations with respect to the sample and detecting the intensities of the resulting diffraction orders for each orientation. CD metrology based on T-SAXS involves determining the dimensions of the sample from the measurements by regression of a predetermined geometric model with the measured data.

In one aspect, T-SAXS measurements of a particular inspection area are performed at a number of different orientations in accordance with a sampling plan. The sampling plan includes a non-uniform spacing of orientations that are more densely concentrated near the normal incidence angle and less densely concentrated at orientations that are further from the normal incidence angle.

In another further aspect, a metrology system is configured to generate a structural model (e.g., geometric model, material model, or combined geometric and material model) of a measured structure of a specimen, generate a T-SAXS response model that includes at least one geometric parameter from the structural model, and resolve at least one specimen parameter value by performing a fitting analysis of T-SAXS measurement data with the T-SAXS response model. In this manner, a comparison of simulated T-SAXS signals with measured data enables the determination of geometric as well as material properties such as electron density and elemental identification and composition of the sample.

In further aspect, an initial estimate of values of one or more parameters of interest is determined based on T-SAXS measurements performed at a single orientation of the incident x-ray beam with respect to the measurement target. The initial, estimated values are implemented as the starting values of the parameters of interest for a regression of the measurement model with measurement data collected from T-SAXS measurements at multiple orientations. In this manner, a close estimate of a parameter of interest is determined with a relatively small amount of computational effort, and by implementing this close estimate as the starting point for a regression over a much larger data set, a refined estimate of the parameter of interest is obtained with less overall computational effort.

In a further aspect, T-SAXS measurement data is used to generate an image of a measured structure based on the measured intensities of the detected diffraction orders. In some embodiments, a T-SAXS response function model is generalized to describe the scattering from a generic electron density mesh. Matching this model to the measured signals, while constraining the modelled electron densities in this mesh to enforce continuity and sparse edges, provides a three dimensional image of the sample.

In a further aspect, a metrology system is configured to generate models for combined x-ray and optical measurement analysis.

The foregoing is a summary and thus contains, by necessity, simplifications, generalizations and omissions of detail; consequently, those skilled in the art will appreciate that the summary is illustrative only and is not limiting in any way. Other aspects, inventive features, and advantages of the devices and/or processes described herein will become apparent in the non-limiting detailed description set forth herein.

DETAILED DESCRIPTION

Reference will now be made in detail to background examples and some embodiments of the invention, examples of which are illustrated in the accompanying drawings.

Methods and systems for characterizing dimensions and material properties of high aspect ratio, vertically manufactured devices using transmission, small-angle x-ray scattering (T-SAXS) techniques are described herein. Such systems and techniques are employed to measure structural and material characteristics associated with different semiconductor fabrication processes. In some examples, T-SAXS is employed to measure critical dimensions, thicknesses, overlay, and material properties of high aspect ratio semiconductor structures including, but not limited to, spin transfer torque random access memory (STT-RAM), three dimensional NAND memory (3D-NAND) or vertical NAND memory (V-NAND), dynamic random access memory (DRAM), three dimensional FLASH memory (3D-FLASH), resistive random access memory (Re-RAM), and phase change random access memory (PC-RAM).

A T-SAXS measurement involves illuminating a sample with an X-ray beam and detecting the intensities of the resulting diffraction orders for one or more angles of incidence relative to the sample. CD metrology based on T-SAXS involves determining the dimensions of the sample from the measurements by regression of a pre-determined geometric model with the measured data. The geometric model includes a few (on the order of ten) adjustable parameters and is representative of the geometry and optical properties of the specimen.

In one aspect, T-SAXS measurements are performed over a range of angles of incidence that provide sufficient resolution and depth of penetration to characterize high aspect ratio structures through their entire depth. The inventors have discovered that x-ray diffracted signals are affected in a strong and unique way when measurements are made at one or more non-normal orientations of the illuminating x-ray beam relative to the plane of the semiconductor wafer, and particularly at orientations near normal incidence.

The use of high brightness T-SAXS enables high flux x-ray radiation penetration into opaque areas of the target. Examples of measureable geometric parameters using T-SAXS includes pore size, pore density, line edge roughness, line width roughness, side wall angle, profile, critical dimension, overlay, edge placement error, and pitch. An example of a measureable material parameter includes electron density. In some examples, T-SAXS enables the measurement of features smaller than 10 nm as well as advanced semiconductor structures such as STT-RAM, V-NAND, DRAM, PC-RAM and Re-RAM, where measurements of geometrical parameters and material parameters are needed.

Figure 1:
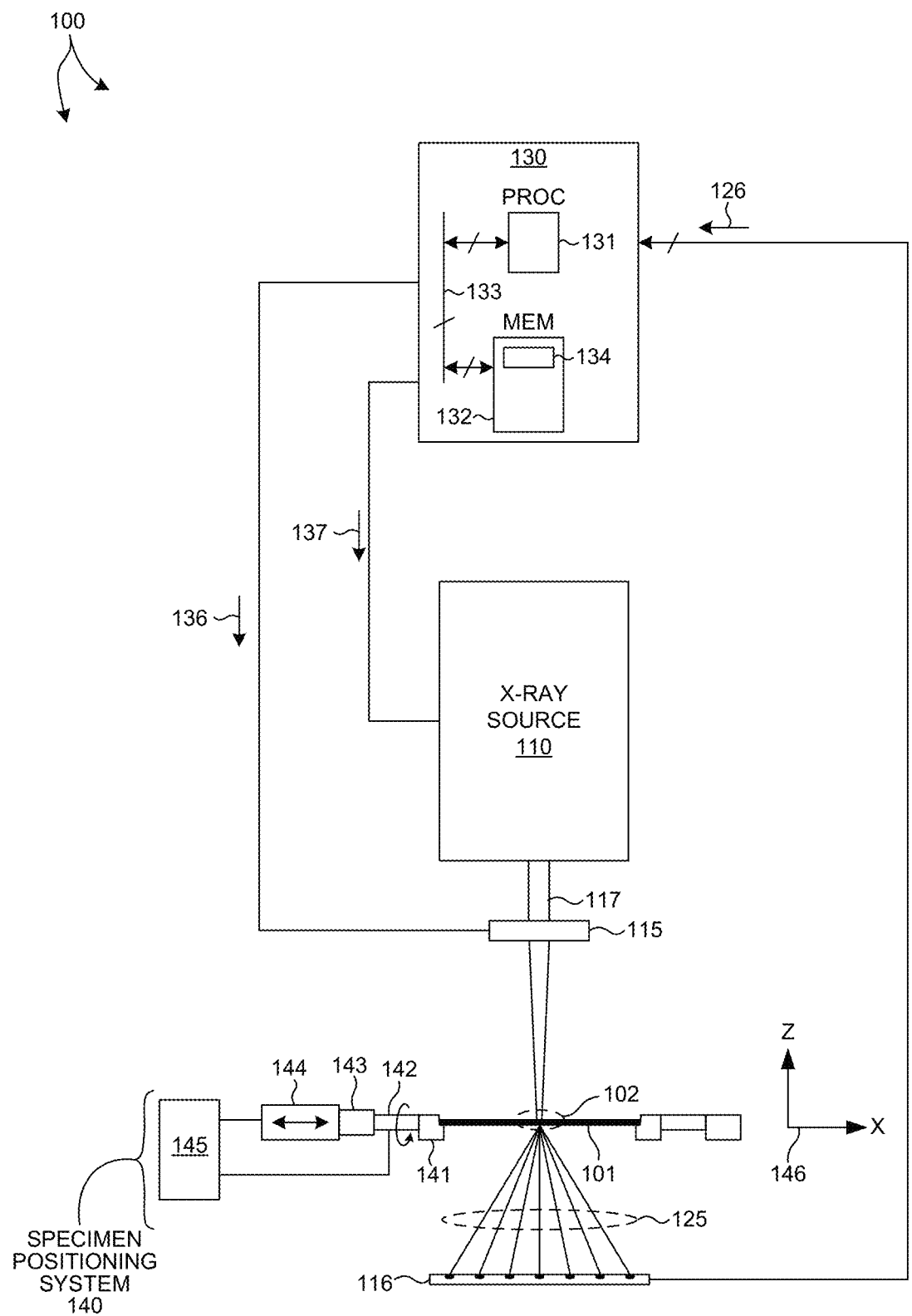
FIG. 1 is a diagram illustrative of a metrology system 100 configured to perform transmission, small-angle x-ray scatterometry (T-SAXS) measurements in accordance with the methods described herein.

FIG. 1 illustrates an embodiment of a metrology tool 100 for measuring characteristics of a specimen in accordance with the exemplary methods presented herein. As shown in FIG. 1, the system 100 may be used to perform T-SAXS measurements over an inspection area 102 of a specimen 101 disposed on a specimen positioning system 140. In some embodiments, the inspection area 102 has a spot size of eighty micrometers or less. In some embodiments, the inspection area 102 has a spot size of fifty micrometers or less. In some embodiments, the inspection area 102 has a spot size of forty micrometers or less.

In the depicted embodiment, metrology tool 100 includes an x-ray illumination source 110 configured to generate x-ray radiation suitable for SAXS measurements. In some embodiments, the x-ray illumination system 110 is configured to generate wavelengths between 0.01 nanometers and 1 nanometer. X-ray illumination source 110 produces an x-ray beam 117 incident on inspection area 102 of specimen 101.

In general, any suitable high-brightness x-ray illumination source capable of generating high brightness x-rays at flux levels sufficient to enable high-throughput, inline metrology may be contemplated to supply x-ray illumination for T-SAXS measurements. In some embodiments, an x-ray source includes a tunable monochromator that enables the x-ray source to deliver x-ray radiation at different, selectable wavelengths.

In some embodiments, one or more x-ray sources emitting radiation with photon energy greater than 15 keV are employed to ensure that the x-ray source supplies light at wavelengths that allow sufficient transmission through the entire device as well as the wafer substrate. By way of non-limiting example, any of a particle accelerator source, a liquid anode source, a rotating anode source, a stationary, solid anode source, a microfocus source, a microfocus rotating anode source, and an inverse Compton source may be employed as x-ray source 110. In one example, an inverse Compton source available from Lyncean Technologies, Inc., Palo Alto, Calif. (USA) may be contemplated. Inverse Compton sources have an additional advantage of being able to produce x-rays over a range of photon energies, thereby enabling the x-ray source to deliver x-ray radiation at different, selectable wavelengths.

Figure 2:
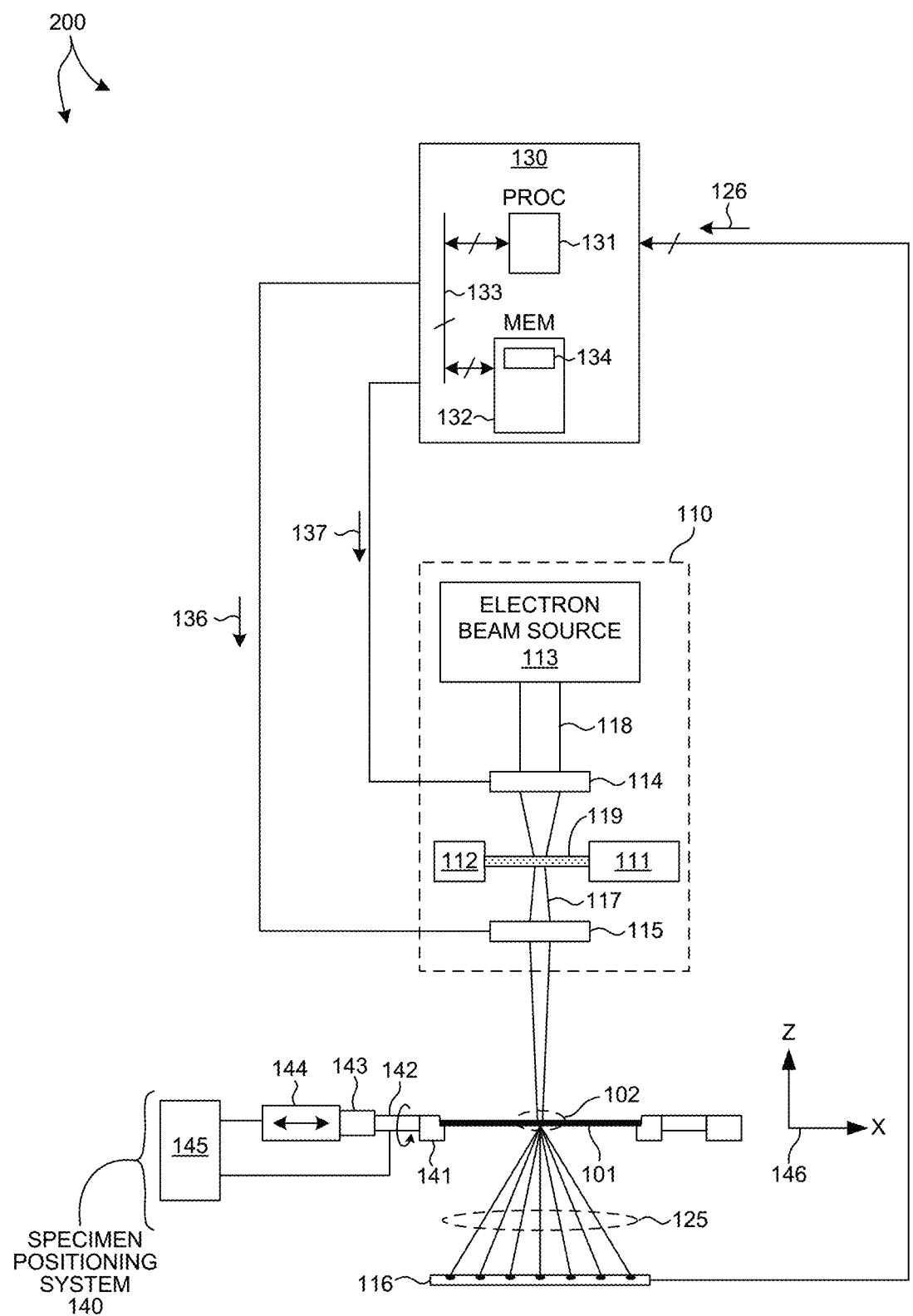
FIG. 2 is a diagram illustrative of a metrology system 200 in another embodiment configured to perform T-SAXS measurements in accordance with the methods described herein.

Exemplary x-ray sources include electron beam sources configured to bombard solid or liquid targets to stimulate x-ray radiation. FIG. 2 depicts a metrology tool 200 for measuring characteristics of a specimen in accordance with the exemplary methods presented herein. Like numbered elements of metrology tool 100 and 200 are analogous. However, in the embodiment depicted in FIG. 2, x-ray illumination source 110 is a liquid metal based x-ray illumination system. A jet of liquid metal 119 is produced from a liquid metal container 111 and collected in a liquid metal collector 112. A liquid metal circulation system (not shown) returns liquid metal collected by collector 112 to liquid metal container 111. The jet of liquid metal 119 includes one or more elements. By way of non-limiting example, the jet of liquid metal 119 includes any of Aluminum, Gallium, Indium, Tin, Thallium, and Bismuth. In this manner, the jet of liquid metal 119 produces x-ray lines corresponding with its constituent elements. In one embodiment, the jet of liquid metal includes a Gallium and Indium alloy. In some embodiments, the x-ray illumination system 110 is configured to generate wavelengths between 0.01 nanometers and 1 nanometer. An electron beam source 113 (e.g., electron gun) produces a stream of electrons 118 that is directed by electron optics 114 to the jet of liquid metal 119. Suitable electron optics 114 includes electromagnets, permanent magnets, or a combination of electromagnets and permanent magnets for focusing the electron beam and directing the beam at the liquid metal jet. The coincidence of the jet of liquid metal 119 and the stream of electrons 118 produces an x-ray beam 117 incident on inspection area 102 of specimen 101.

In one embodiment, the incident x-ray beam 117 is at the Indium ka line of 24.2 keV. The x-ray beam is collimated down to less than one milliradian divergence using multi-layer x-ray optics for T-SAXS measurements.

In some embodiments, the x-ray scattering measurements described herein are achieved without using a screen located between the x-ray source and the specimen under measurement. In these embodiments, the measured intensities of the diffraction orders over a range of angles of incidence, multiple wavelengths, or a combination of both, provide sufficient information to resolve a distribution map (i.e., image) of a desired material property (e.g., complex refractive index, electron density, or absorptivity) of the measured structure. However, in some other examples, a pinhole or another aperture is located on an otherwise opaque screen that is located between the x-ray source and the specimen under measurement to improve collimation of the x-ray beam. The intensity of the diffraction pattern is measured for several positions of the aperture. In some other embodiments, a screen with a pseudo-random aperture pattern is used, and the diffraction pattern is measured for multiple screens. These approaches may also be contemplated to provide additional information to resolve the three-dimensional distribution of the desired material property of the measured structure.

Methods and systems for generating high brightness, liquid metal x-ray illumination are described in U.S. Pat. No. 7,929,667, issued on Apr. 19, 2011, to KLA-Tencor Corp., the entirety of which is incorporated herein by reference.

As depicted in FIG. 1, x-ray optics 115 shape and direct incident x-ray beam 117 to specimen 101. In some examples, x-ray optics 115 include an x-ray monochromator to monochromatize the x-ray beam that is incident on the specimen 101. In one example, a crystal monochromator such as a Loxley-Tanner-Bowen monochromator is employed to monochromatize the beam of x-ray radiation. In some examples, x-ray optics 115 collimate or focus the x-ray beam 117 onto inspection area 102 of specimen 101 to less than 1 milliradian divergence using multilayer x-ray optics. In some embodiments, x-ray optics 115 includes one or more x-ray collimating mirrors, x-ray apertures, x-ray beam stops, refractive x-ray optics, diffractive optics such as zone plates, specular x-ray optics such as grazing incidence ellipsoidal mirrors, polycapillary optics such as hollow capillary x-ray waveguides, multilayer optics, or systems, or any combination thereof. Further details are described in U.S. Patent Publication No. 2015/0110249, the content of which is incorporated herein by reference it its entirety.

X-ray detector 116 collects x-ray radiation 125 scattered from specimen 101 and generates an output signal 126 indicative of properties of specimen 101 that are sensitive to the incident x-ray radiation in accordance with a T-SAXS measurement modality. In some embodiments, scattered x-rays 125 are collected by x-ray detector 116 while specimen positioning system 140 locates and orients specimen 101 to produce angularly resolved scattered x-rays. In some embodiments, the x-ray detector 116 is able to resolve one or more x-ray photon energies and produces signals for each x-ray energy component indicative of properties of the specimen. In some embodiments, the x-ray detector 116 includes any of a CCD array, a microchannel plate, a photodiode array, a microstrip proportional counter, a gas filled proportional counter, a scintillator, or a fluorescent material. In some embodiments, the x-ray detector 116 includes a single photon counting detector that detects the position and number of detected photons.

In some embodiments, x-ray detector 116 is maintained in the same atmospheric environment as specimen 101 (e.g., gas purge environment). However, in some embodiments, the distance between specimen 101 and x-ray detector 116 is lengthy (e.g., greater than one meter). In these embodiments, environmental disturbances (e.g., air turbulence) contribute noise to the detected signals. Hence in some embodiments, one or more of the x-ray detectors is maintained in a localized, vacuum environment separated from the specimen (e.g., specimen 101) by a vacuum window.

Figure 3:
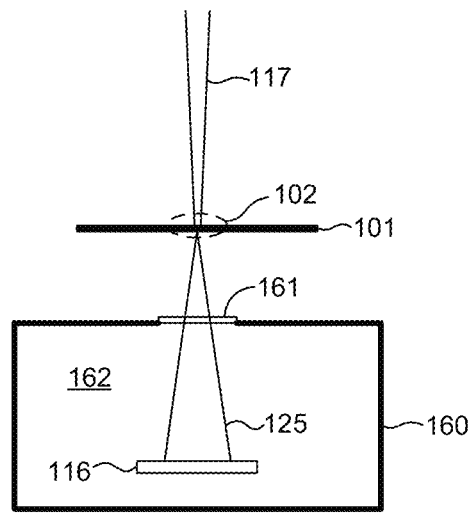
FIG. 3 is a diagram illustrative of a x-ray detector 116 of metrology systems 100 and 200 contained in a vacuum environment 162 separate from specimen 101.

FIG. 3 is a diagram illustrative of a vacuum chamber 160 containing x-ray detector 116 in one embodiment. In a preferred embodiment, vacuum chamber 160 includes a substantial portion of the path between specimen 101 and x-ray detector 116. An opening of vacuum chamber 160 is covered by vacuum window 161. Vacuum window 161 may be constructed of any suitable material that is substantially transparent to x-ray radiation (e.g., Beryllium). Scattered x-ray radiation 125 passes through vacuum window 161, enters vacuum chamber 160 and is incident on x-ray detector 116. A suitable vacuum environment 162 is maintained within vacuum chamber 160 to minimize disturbances to scattered x-ray radiation 125.

Metrology tool 100 also includes a computing system 130 employed to acquire signals 126 generated by SAXS detector 116 and determine properties of the specimen based at least in part on the acquired signals. As illustrated in FIG. 1, computing system 130 is communicatively coupled to SAXS detector 116.

In a T-SAXS measurement, a high aspect ratio, vertically manufactured structure diffracts a collimated X-ray beam into diffraction orders. Each diffraction order travels in a particular, predictable direction. The angular spacing of the diffraction orders is inversely proportional to the lattice constant of the specimen divided by the wavelength. The diffraction orders can be individually detected by a detector array placed at some distance from the wafer. Each pixel of the detector outputs a signal that indicates the number of photons that hit the pixel. Outputs of pixels that belong to the same diffraction order are combined. The intensities of diffraction orders are of the form I(m, n, q, j, λ). {m, n} are integer indices of diffraction orders. {q, j} are azimuth and elevation angles of incidence beam (i.e., polar coordinates of the incident chief ray with respect to a coordinate system that is fixed to the wafer). A is the wavelength of the incident X-ray.

Measurements of the intensity of diffracted radiation as a function of x-ray incidence angle relative to the wafer surface normal are collected. Information contained in the multiple diffraction orders is typically unique between each model parameter under consideration. Thus, x-ray scattering yields estimation results for values of parameters of interest with small errors and reduced parameter correlation.

In another further aspect, computing system 130 is configured to generate a structural model (e.g., geometric model, material model, or combined geometric and material model) of a measured structure of a specimen, generate a T-SAXS response model that includes at least one geometric parameter from the structural model, and resolve at least one specimen parameter value by performing a fitting analysis of T-SAXS measurement data with the T-SAXS response model. The analysis engine is used to compare the simulated T-SAXS signals with measured data thereby allowing the determination of geometric as well as material properties such as electron density of the sample. In the embodiment depicted in FIG. 1, computing system 130 is configured as a model building and analysis engine configured to implement model building and analysis functionality as described herein.

Figure 4:
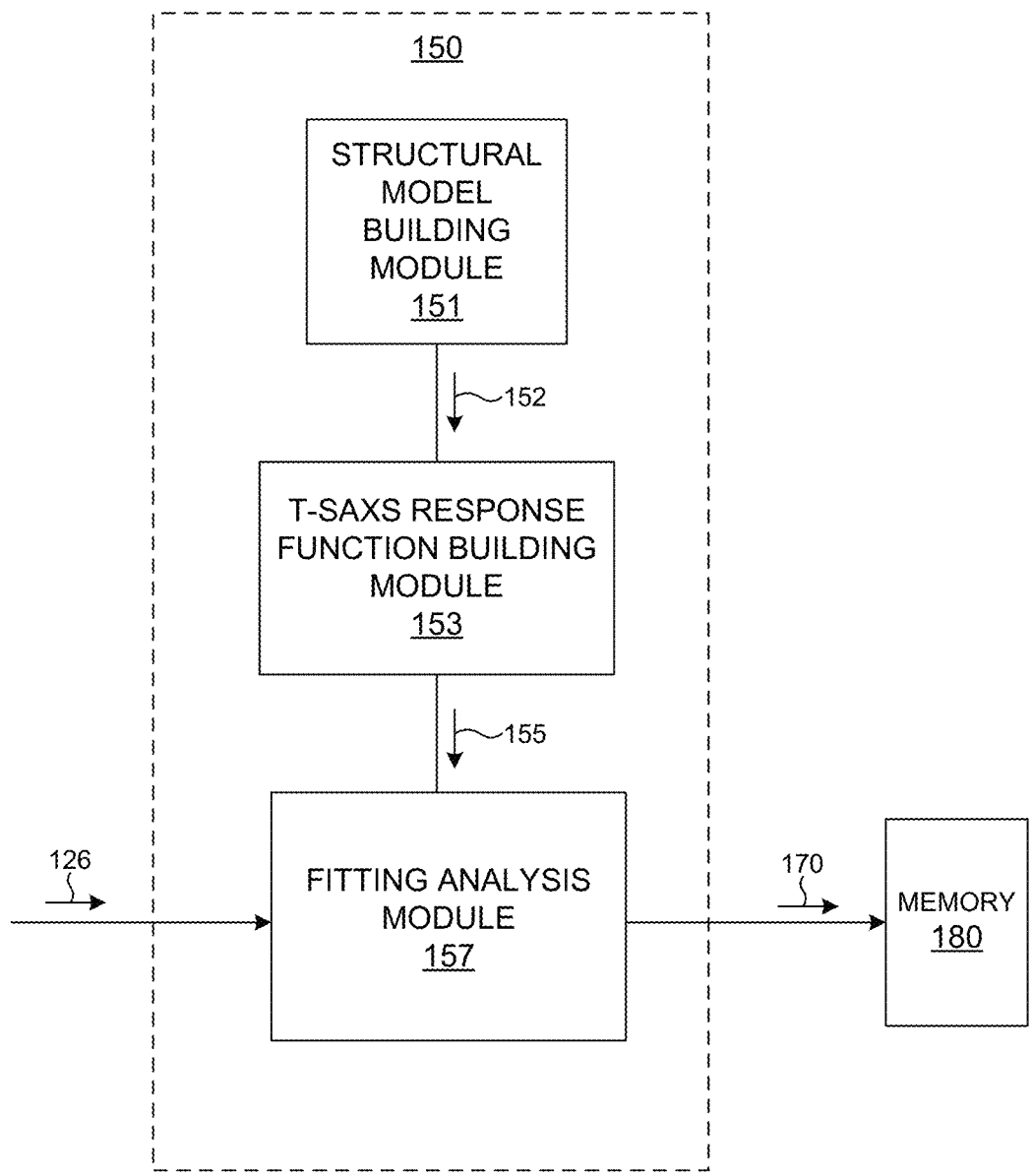
FIG. 4 is a diagram illustrative of a model building and analysis engine 150 configured to resolve specimen parameter values based on T-SAXS data in accordance with the methods described herein.

FIG. 4 is a diagram illustrative of an exemplary model building and analysis engine 150 implemented by computing system 130. As depicted in FIG. 4, model building and analysis engine 150 includes a structural model building module 151 that generates a structural model 152 of a measured structure of a specimen. In some embodiments, structural model 152 also includes material properties of the specimen. The structural model 152 is received as input to T-SAXS response function building module 153. T-SAXS response function building module 153 generates a T-SAXS response function model 155 based at least in part on the structural model 152. In some examples, the T-SAXS response function model 155 is based on x-ray form factors $$F(\vec{q}) = \int \rho(\vec{r}) e^{-i\vec{q}\cdot\vec{r}} d\vec{r} \qquad (1)$$

where F is the form factor, q is the scattering vector, and ρ(r) is the electron density of the specimen in spherical coordinates. The x-ray scattering intensity is then given by $$I(\vec{q}) = F^*F. \qquad (2)$$

T-SAXS response function model 155 is received as input to fitting analysis module 157. The fitting analysis module 157 compares the modeled T-SAXS response with the corresponding measured data to determine geometric as well as material properties of the specimen.

In some examples, the fitting of modeled data to experimental data is achieved by minimizing a chi-squared value. For example, for T-SAXS measurements, a chi-squared value can be defined as $$\chi^2_{SAXS} = \frac{1}{N_{SAXS}} \sum_j^{N_{SAXS}} \frac{\left(S_j^{SAXS\ model}(v_1, \ldots, v_L) - S_j^{SAXS\ experiment}\right)^2}{\sigma^2_{SAXS,j}} \quad (3)$$

Where, $S_j^{SAXS\ experiment}$ is the measured T-SAXS signals 126 in the "channel" j, where the index j describes a set of system parameters such as diffraction order, energy, angular coordinate, etc. $S_j^{SAXS\ model}(v_1, \ldots, v_L)$ is the modeled T-SAXS signal $S_j$ for the "channel" j, evaluated for a set of structure (target) parameters $v_1, \ldots, v_L$, where these parameters describe geometric (CD, sidewall angle, overlay, etc.) and material (electron density, etc.). $\sigma_{SAXS,j}$ is the uncertainty associated with the jth channel. $N_{SAXS}$ is the total number of channels in the x-ray metrology. L is the number of parameters characterizing the metrology target.

Equation (3) assumes that the uncertainties associated with different channels are uncorrelated. In examples where the uncertainties associated with the different channels are correlated, a covariance between the uncertainties, can be calculated. In these examples a chi-squared value for T-SAXS measurements can be expressed as $$\chi^2_{SAXS} = \frac{1}{N_{SAXS}} \left(\vec{S}_j^{SAXS.\ model}(v_1, \ldots, v_M) - \vec{S}_j^{SAXS.\ experiment}\right)^T$$
$$V_{SAXS}^{-1} \left(\vec{S}_j^{SAXS.\ model}(v_1, \ldots, v_M) - \vec{S}_j^{SAXS.\ experiment}\right) \quad (4)$$

where, $V_{SAXS}$ is the covariance matrix of the SAXS channel uncertainties, and T denotes the transpose.

In some examples, fitting analysis module 157 resolves at least one specimen parameter value by performing a fitting analysis on T-SAXS measurement data 126 with the T-SAXS response model 155. In some examples, $\chi^2_{SAXS}$ is optimized.

As described hereinbefore, the fitting of T-SAXS data is achieved by minimization of chi-squared values. However, in general, the fitting of T-SAXS data may be achieved by other functions.

The fitting of T-SAXS metrology data is advantageous for any type of T-SAXS technology that provides sensitivity to geometric and/or material parameters of interest. Specimen parameters can be deterministic (e.g., CD, SWA, etc.) or statistical (e.g., rms height of sidewall roughness, roughness correlation length, etc.) as long as proper models describing T-SAXS beam interaction with the specimen are used.

In general, computing system 130 is configured to access model parameters in real-time, employing Real Time Critical Dimensioning (RTCD), or it may access libraries of pre-computed models for determining a value of at least one specimen parameter value associated with the specimen 101. In general, some form of CD-engine may be used to evaluate the difference between assigned CD parameters of a specimen and CD parameters associated with the measured specimen. Exemplary methods and systems for computing specimen parameter values are described in U.S. Pat. No. 7,826,071, issued on Nov. 2, 2010, to KLA-Tencor Corp., the entirety of which is incorporated herein by reference.

In some examples, model building and analysis engine 150 improves the accuracy of measured parameters by any combination of feed sideways analysis, feed forward analysis, and parallel analysis. Feed sideways analysis refers to taking multiple data sets on different areas of the same specimen and passing common parameters determined from the first dataset onto the second dataset for analysis. Feed forward analysis refers to taking data sets on different specimens and passing common parameters forward to subsequent analyses using a stepwise copy exact parameter feed forward approach. Parallel analysis refers to the parallel or concurrent application of a non-linear fitting methodology to multiple datasets where at least one common parameter is coupled during the fitting.

Multiple tool and structure analysis refers to a feed forward, feed sideways, or parallel analysis based on regression, a look-up table (i.e., "library" matching), or another fitting procedure of multiple datasets. Exemplary methods and systems for multiple tool and structure analysis is described in U.S. Pat. No. 7,478,019, issued on Jan. 13, 2009, to KLA-Tencor Corp., the entirety of which is incorporated herein by reference.

In one further aspect, metrology tool 100 includes a computing system (e.g., computing system 130) configured to implement beam control functionality as described herein. In the embodiment depicted in FIG. 1, computing system 130 is configured as a beam controller operable to control any of the illumination properties such as intensity, divergence, spot size, polarization, spectrum, and positioning of the incident SAXS illumination beam 117.

As illustrated in FIG. 1, computing system 130 is communicatively coupled to SAXS detector 116. Computing system 130 is configured to receive measurement data 126 from SAXS detector 116. In one example, measurement data 126 includes an indication of the measured SAXS response of the specimen (i.e., intensities of the diffraction orders). Based on the distribution of the measured SAXS response on the surface of detector 116, the location and area of incidence of SAXS illumination beam 117 on specimen 101 is determined by computing system 130. In one example, pattern recognition techniques are applied by computing system 130 to determine the location and area of incidence of SAXS illumination beam 117 on specimen 101 based on measurement data 126. In some examples, computing system 130 communicates command signal 137 to illumination optics 115 to select the desired illumination wavelength and redirect and reshape SAXS illumination beam 117 such that incident SAXS illumination beam 117 arrives at the desired location and angular orientation with respect to specimen 101. In some other examples, computing system 130 communicates a command signal to wafer positioning system 140 to position and orient specimen 101 such that incident SAXS illumination beam 117 arrives at the desired location and angular orientation with respect to specimen 101. In some other examples, computing system 130 communicates a command signal 137 to x-ray source 110 to select the desired illumination wavelength and redirect and reshape SAXS illumination beam 117 such that incident SAXS illumination beam 117 arrives at the desired location and angular orientation with respect to specimen 101.

In one aspect, T-SAXS measurements of a particular inspection area are performed at a number of different orientations in accordance with a sampling plan. In one further aspect, the sampling plan includes a non-uniform spacing of orientations that are more densely concentrated near the normal incidence angle (e.g., within a range within four degrees of the normal to the wafer surface) and less densely concentrated at orientations that are further from the normal incidence angle (e.g., within a range between ten degrees and forty degrees from the normal angle).

In some embodiments, it is desirable to perform measurements at different orientations described by rotations about the x and y axes indicated by coordinate system 146 depicted in FIG. 1. This increases the precision and accuracy of measured parameters and reduces correlations among parameters by extending the number and diversity of data sets available for analysis to include a variety of large-angle, out of plane orientations. Measuring specimen parameters with a deeper, more diverse data set also reduces correlations among parameters and improves measurement accuracy. For example, in a normal orientation, SAXS is able to resolve the critical dimension of a feature, but is largely insensitive to sidewall angle and height of a feature. However, by collecting measurement data over a broad range of out of plane angular positions, the sidewall angle and height of a feature can be resolved.

As illustrated in FIG. 1, metrology tool 100 includes a specimen positioning system 140 configured to both align specimen 101 and orient specimen 101 over a large range of out of plane angular orientations with respect the SAXS scatterometer. In other words, specimen positioning system 140 is configured to rotate specimen 101 over a large angular range about one or more axes of rotation aligned in-plane with the surface of specimen 101. In some embodiments, specimen positioning system 140 is configured to rotate specimen 101 within a range of at least 90 degrees about one or more axes of rotation aligned in-plane with the surface of specimen 101. In some embodiments, specimen positioning system is configured to rotate specimen 101 within a range of at least 60 degrees about one or more axes of rotation aligned in-plane with the surface of specimen 101. In some other embodiments, specimen positioning system is configured to rotate specimen 101 within a range of at least one degree about one or more axes of rotation aligned in-plane with the surface of specimen 101. In this manner, angle resolved measurements of specimen 101 are collected by metrology system 100 over any number of locations on the surface of specimen 101. In one example, computing system 130 communicates command signals to motion controller 145 of specimen positioning system 140 that indicate the desired position of specimen 101. In response, motion controller 145 generates command signals to the various actuators of specimen positioning system 140 to achieve the desired positioning of specimen 101.

By way of non-limiting example, as illustrated in FIG. 1, specimen positioning system 140 includes an edge grip chuck 141 to fixedly attach specimen 101 to specimen positioning system 140. A rotational actuator 142 is configured to rotate edge grip chuck 141 and the attached specimen 101 with respect to a perimeter frame 143. In the depicted embodiment, rotational actuator 142 is configured to rotate specimen 101 about the x-axis of the coordinate system 146 illustrated in FIG. 1. As depicted in FIG. 1, a rotation of specimen 101 about the z-axis is an in plane rotation of specimen 101. Rotations about the x-axis and the y-axis (not shown) are out of plane rotations of specimen 101 that effectively tilt the surface of the specimen with respect to the metrology elements of metrology system 100. Although it is not illustrated, a second rotational actuator is configured to rotate specimen 101 about the y-axis. A linear actuator 144 is configured to translate perimeter frame 143 in the x-direction. Another linear actuator (not shown) is configured to translate perimeter frame 143 in the y-direction. In this manner, every location on the surface of specimen 101 is available for measurement over a range of out of plane angular positions. For example, in one embodiment, a location of specimen 101 is measured over several angular increments within a range of −45 degrees to +45 degrees with respect to the normal orientation of specimen 101.

In general, specimen positioning system 140 may include any suitable combination of mechanical elements to achieve the desired linear and angular positioning performance, including, but not limited to goniometer stages, hexapod stages, angular stages, and linear stages.

In further aspect, an initial estimate of values of one or more parameters of interest is determined based on T-SAXS measurements performed at a single orientation of the incident x-ray beam with respect to the measurement target. The initial, estimated values are implemented as the starting values of the parameters of interest for a regression of the measurement model with measurement data collected from T-SAXS measurements at multiple orientations. In this manner, a close estimate of a parameter of interest is determined with a relatively small amount of computational effort, and by implementing this close estimate as the starting point for a regression over a much larger data set, a refined estimate of the parameter of interest is obtained with less overall computational effort.

In a further aspect, T-SAXS measurement data is used to generate an image of a measured structure based on the measured intensities of the detected diffraction orders. In some embodiments, a T-SAXS response function model is generalized to describe the scattering from a generic electron density mesh. Matching this model to the measured signals, while constraining the modelled electron densities in this mesh to enforce continuity and sparse edges, provides a three dimensional image of the sample.

Although, geometric, model-based, parametric inversion is preferred for critical dimension (CD) metrology based on T-SAXS measurements, a map of the specimen generated from the same T-SAXS measurement data is useful to identify and correct model errors when the measured specimen deviates from the assumptions of the geometric model.

In some examples, the image is compared to structural characteristics estimated by a geometric, model-based parametric inversion of the same scatterometry measurement data. Discrepancies are used to update the geometric model of the measured structure and improve measurement performance. The ability to converge on an accurate parametric measurement model is particularly important when measuring integrated circuits to control, monitor, and trouble-shoot their manufacturing process.

In some examples, the image is a two dimensional (2-D) map of electron density, absorptivity, complex index of refraction, or a combination of these material characteristics. In some examples, the image is a three dimensional (3-D) map of electron density, absorptivity, complex index of refraction, or a combination of these material characteristics. The map is generated using relatively few physical constraints. In some examples, one or more parameters of interest, such as critical dimension (CD), sidewall angle (SWA), overlay, edge placement error, pitch walk, etc., are estimated directly from the resulting map. In some other examples, the map is useful for debugging the wafer process when the sample geometry or materials deviate outside the range of expected values contemplated by a parametric structural model employed for model-based CD measurement. In one example, the differences between the map and a rendering of the structure predicted by the parametric structural model according to its measured parameters are used to update the parametric structural model and improve its measurement performance. Further details are described in U.S. Patent Publication No. 2015/0300965, the content of which is incorporated herein by reference it its entirety. Additional details are described in U.S. Patent Publication No. 2015/0117610, the content of which is incorporated herein by reference it its entirety.

In a further aspect, model building and analysis engine 150 is employed to generate models for combined x-ray and optical measurement analysis. In some examples, optical simulations are based on, e.g., rigorous coupled-wave analysis (RCWA) where Maxwell's equations are solved to calculate optical signals such as reflectivities for different polarizations, ellipsometric parameters, phase change, etc.

Values of one or more parameters of interest are determined based on a combined fitting analysis of the detected intensities of the x-ray diffraction orders at the plurality of different angles of incidence and detected optical intensities with a combined, geometrically parameterized response model. The optical intensities are measured by an optical metrology tool that may or may not be mechanically integrated with an x-ray metrology system, such as systems 100 and 200 depicted in FIGS. 1 and 2, respectively. Further details are described in U.S. Patent Publication No. 2014/0019097 and U.S. Patent Publication No. 2013/0304424, the contents of each are incorporated herein by reference it their entirety.

Figure 6:
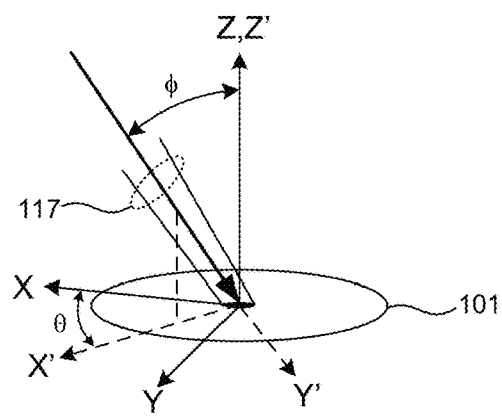
FIG. 6 depicts x-ray illumination beam 117 incident on wafer 101 at a particular orientation described by angles $\phi$ and $\theta$.

As described herein, T-SAXS measurements are performed at multiple orientations of the illuminating x-ray beam relative to the surface normal of the semiconductor wafer. Each orientation is described by any two angular rotations of wafer 101 with respect to the x-ray illumination beam, or vice-versa. In one example, the orientation can be described with respect to a coordinate system fixed to the wafer. FIG. 6 depicts x-ray illumination beam 117 incident on wafer 101 at a particular orientation described by angles $\phi$ and $\theta$. Coordinate frame XYZ is fixed the metrology system and coordinate frame X'Y'Z' is fixed to wafer 101. Z is aligned with an axis normal to the surface of wafer 101. X and Y are in a plane aligned with the surface of wafer 101. Similarly, Z' is aligned with an axis normal to the surface of wafer 101, and X' and Y' are in a plane aligned with the surface of wafer 101. As depicted in FIG. 6, x-ray illumination beam 117 lies within the X'Z' plane. Angle, $\phi$, describes the orientation of the x-ray illumination beam 117 with respect to the surface normal of the wafer in the X'Z' plane. Furthermore, angle, $\theta$, describes the orientation of the X'Z' plane with respect to the XZ plane. Together, $\theta$ and $\phi$, uniquely define the orientation of the x-ray illumination beam 117 with respect to the surface of wafer 101. In this example, the orientation of the x-ray illumination beam with respect to the surface of wafer 101 is described by a rotation about an axis normal to the surface of wafer 101 (i.e., Z axis) and a rotation about an axis aligned with the surface of wafer 101 (i.e., Y' axis). In some other examples, the orientation of the x-ray illumination beam with respect to the surface of wafer 101 is described by a rotation about a first axis aligned with the surface of wafer 101 and another axis aligned with the surface of wafer 101 and perpendicular to the first axis as described with reference to FIG. 1.

In some embodiments, the metrology target characterized T-SAXS measurements as described herein is located within a scribe line of the wafer under measurement. In these embodiments, the metrology target is sized to fit within the width of the scribe line. In some examples, the scribe line width is less than eighty micrometers. In some examples, the scribe line is less than fifty micrometers. In general, the width of the scribe lines employed in semiconductor manufacturing is trending smaller.

In some embodiments, the metrology target characterized T-SAXS measurements as described herein is located within an active die area of the wafer under measurement and is a part of a functional integrated circuit (e.g., memory, image sensor, logic device, etc.).

In general, it is preferred that the illumination beam spot size closely match the lateral dimensions of the metrology target under measurement to minimize contamination signals from structures surrounding the metrology target under measurement. In some embodiments, the metrology target under measurement is less than 70 micrometers in any lateral dimension. In some embodiments, the metrology target under measurement is less than 50 micrometers in any lateral dimension. In some embodiments, the metrology target under measurement is less than 40 micrometers in any lateral dimension. In some embodiments, the metrology target under measurement is less than 10 micrometers in any lateral dimension. In some embodiments, the metrology target under measurement is characterized by an overall height (or equivalently, depth) of more than one micrometer. In some embodiments, the metrology target under measurement is characterized by an overall height (or equivalently, depth) of more than two micrometers.

In general, a metrology target is characterized by an aspect ratio defined as a maximum height dimension (i.e., dimension normal to the wafer surface) divided by a maximum lateral extent dimension (i.e., dimension aligned with the wafer surface) of the metrology target. In some embodiments, the metrology target under measurement has an aspect ratio of at least twenty. In some embodiments, the metrology target has an aspect ratio of at least forty.

Figure 5A:
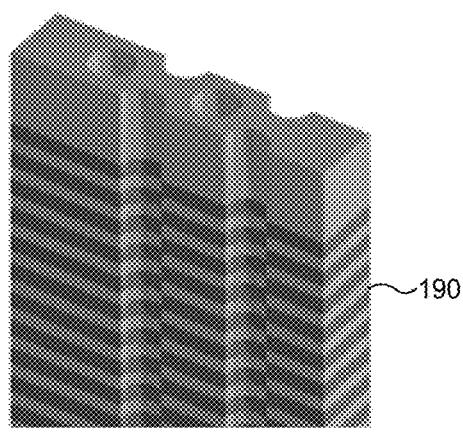
FIGS. 5A-5C depict an isometric view, a top view, and a cross-sectional view, respectively, of a typical 3D FLASH memory device 190 subject to measurement in the manner described herein.
Figure 5B:
Figure 5C:
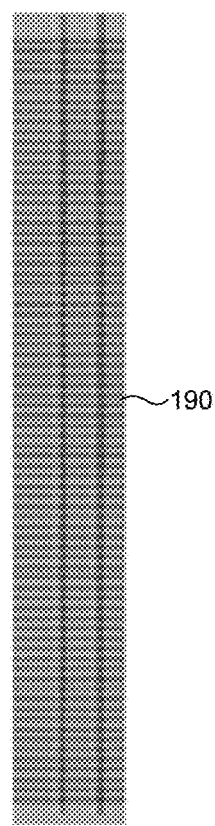

FIGS. 5A-5C depict an isometric view, a top view, and a cross-sectional view, respectively, of a typical 3D FLASH memory device 190 subject to measurement in the manner described herein. The total height (or equivalently depth) of memory device 190 ranges from one to several micrometers. Memory device 190 is a vertically manufactured device. A vertically manufactured device, such as memory device 190, essentially turns a conventional, planar memory device 90 degrees, orienting the bit line and cell string vertically (perpendicular to wafer surface). To provide sufficient memory capacity, a large number of alternating layers of different materials are deposited on the wafer. This requires patterning processes to perform well to depths of several microns for structures with a maximum lateral extent of one hundred nanometers or less. As a result, aspect ratios of 25 to 1 or 50 to 1 are not uncommon.

Figure 7:
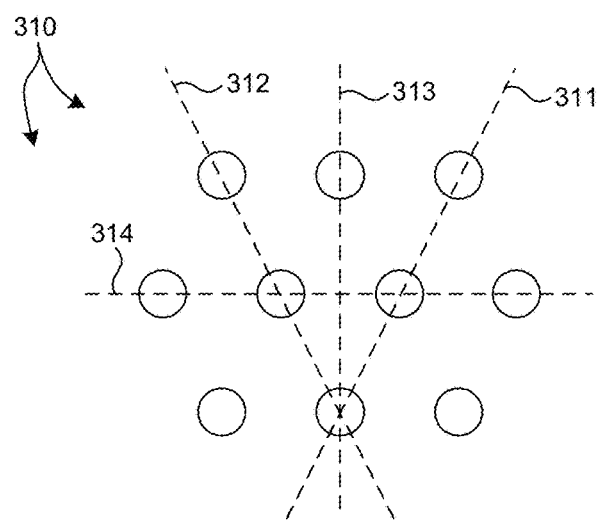
FIG. 7 depicts a top view of an array of high aspect ratio hole structures 310.

FIG. 7 depicts a top view of an array of high aspect ratio hole structures 310. As depicted in FIG. 7, the array of hole structures are most closely patterned along planes 311, 312, 313, and 314 (which extend inward and outward from the drawing). In some embodiments, it is preferred to perform measurements of high aspect ratio structures as described herein at orientations of the incident x-ray illumination beam with respect to the surface of the wafer under measurement that lie within planes where an array of high aspect ratio structures are most closely patterned. In the example depicted in FIG. 7, it is preferred to provide x-ray illumination to the array of hole structures 310 within planes 311 and 312, and 313 and 314, where the array of hole structures are most closely patterned.

Figures 8A, 8B, 8C:
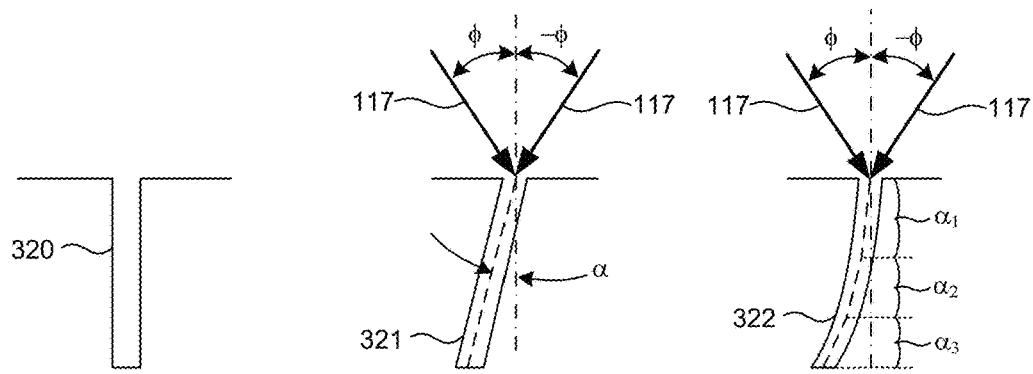
FIG. 8A depicts a side view of an ideal high aspect ratio hole structure 320.
FIG. 8B depicts a side view of a tilted hole structure 321.
FIG. 8C depicts a side view of a progressively tilted hole structure 322, where the degree of tilt progressively increases with depth.

FIG. 8A depicts a side view of an ideal high aspect ratio hole structure 320. FIG. 8B depicts a side view of a tilted hole structure 321. FIG. 8C depicts a side view of a progressively tilted hole structure 322, where the degree of tilt progressively increases with depth. In many examples, hole structures 321 and 322 are undesirable. In some embodiments, hole structures resembling hole structures 321 and 322 are characterized by T-SAXS measurements as described herein. In one example, hole structure 321 is characterized by a tilt angle parameter, $\alpha$. Furthermore, x-ray illumination beam 117 is provided to hole structure 321 at an angle, $\phi$, with respect to the surface normal, and at the opposite angle, $-\phi$, as described, for example, with reference to FIG. 6. In some embodiments, differences in measured T-SAX signals that arise in these two illumination scenarios provide sufficient signal information to accurately estimate the tilt angle, $\alpha$.

In another example, hole structure 322 is piecewise characterized by a number of tilt angle parameter, $\alpha_1$, $\alpha_2$, and $\alpha_3$. Similarly, x-ray illumination beam 117 is provided to hole structure 322 at an angle, $\phi$, with respect to the surface normal, and at the opposite angle, $-\phi$, as described, for example, with reference to FIG. 6. In some embodiments, differences in measured T-SAX signals that arise in these two illumination scenarios provide sufficient signal information to accurately estimate the tilt angles, $\alpha_1$, $\alpha_2$, and $\alpha_3$.

It should be recognized that the various steps described throughout the present disclosure may be carried out by a single computer system 130 or, alternatively, a multiple computer system 130. Moreover, different subsystems of the system 100, such as the specimen positioning system 140, may include a computer system suitable for carrying out at least a portion of the steps described herein. Therefore, the aforementioned description should not be interpreted as a limitation on the present invention but merely an illustration. Further, the one or more computing systems 130 may be configured to perform any other step(s) of any of the method embodiments described herein.

In addition, the computer system 130 may be communicatively coupled to the SAXS detector 116 and the SAXS illumination optics 115 in any manner known in the art. For example, the one or more computing systems 130 may be coupled to computing systems associated with the SAXS detector 116 and the SAXS illumination optics 115, respectively. In another example, any of the SAXS detector 116 and the SAXS illumination optics 115 may be controlled directly by a single computer system coupled to computer system 130.

The computer system 130 may be configured to receive and/or acquire data or information from the subsystems of the system (e.g., SAXS detector 116 and SAXS illumination optics 115, and the like) by a transmission medium that may include wireline and/or wireless portions. In this manner, the transmission medium may serve as a data link between the computer system 130 and other subsystems of the system 100.

Computer system 130 of the metrology system 100 may be configured to receive and/or acquire data or information (e.g., measurement results, modeling inputs, modeling results, etc.) from other systems by a transmission medium that may include wireline and/or wireless portions. In this manner, the transmission medium may serve as a data link between the computer system 130 and other systems (e.g., memory on-board metrology system 100, external memory, or external systems). For example, the computing system 130 may be configured to receive measurement data (e.g., signals 126) from a storage medium (i.e., memory 132 or 180) via a data link. For instance, spectral results obtained using a spectrometer of any of SAXS detector 116 may be stored in a permanent or semi-permanent memory device (e.g., memory 132 or 180). In this regard, the measurement results may be imported from on-board memory or from an external memory system. Moreover, the computer system 130 may send data to other systems via a transmission medium. For instance, specimen parameter values 170 determined by computer system 130 may be stored in a permanent or semi-permanent memory device (e.g., memory 180). In this regard, measurement results may be exported to another system.

Computing system 130 may include, but is not limited to, a personal computer system, mainframe computer system, workstation, image computer, parallel processor, or any other device known in the art. In general, the term "computing system" may be broadly defined to encompass any device having one or more processors, which execute instructions from a memory medium.

Program instructions 134 implementing methods such as those described herein may be transmitted over a transmission medium such as a wire, cable, or wireless transmission link. For example, as illustrated in FIG. 1, program instructions stored in memory 132 are transmitted to processor 131 over bus 133. Program instructions 134 are stored in a computer readable medium (e.g., memory 132). Exemplary computer-readable media include read-only memory, a random access memory, a magnetic or optical disk, or a magnetic tape.

In some embodiments, a scatterometry analysis as described herein is implemented as part of a fabrication process tool. Examples of fabrication process tools include, but are not limited to, lithographic exposure tools, film deposition tools, implant tools, and etch tools. In this manner, the results of a T-SAXS analysis are used to control a fabrication process. In one example, T-SAXS measurement data collected from one or more targets is sent to a fabrication process tool. The T-SAXS measurement data is analyzed as described herein and the results used to adjust the operation of the fabrication process tool.

Scatterometry measurements as described herein may be used to determine characteristics of a variety of semiconductor structures. Exemplary structures include, but are not limited to, FinFETs, low-dimensional structures such as nanowires or graphene, sub 10 nm structures, lithographic structures, through substrate vias (TSVs), memory structures such as DRAM, DRAM 4F2, FLASH, MRAM and high aspect ratio memory structures. Exemplary structural characteristics include, but are not limited to, geometric parameters such as line edge roughness, line width roughness, pore size, pore density, side wall angle, profile, critical dimension, pitch, and material parameters such as electron density, composition, grain structure, morphology, stress, strain, and elemental identification.

Figure 9:
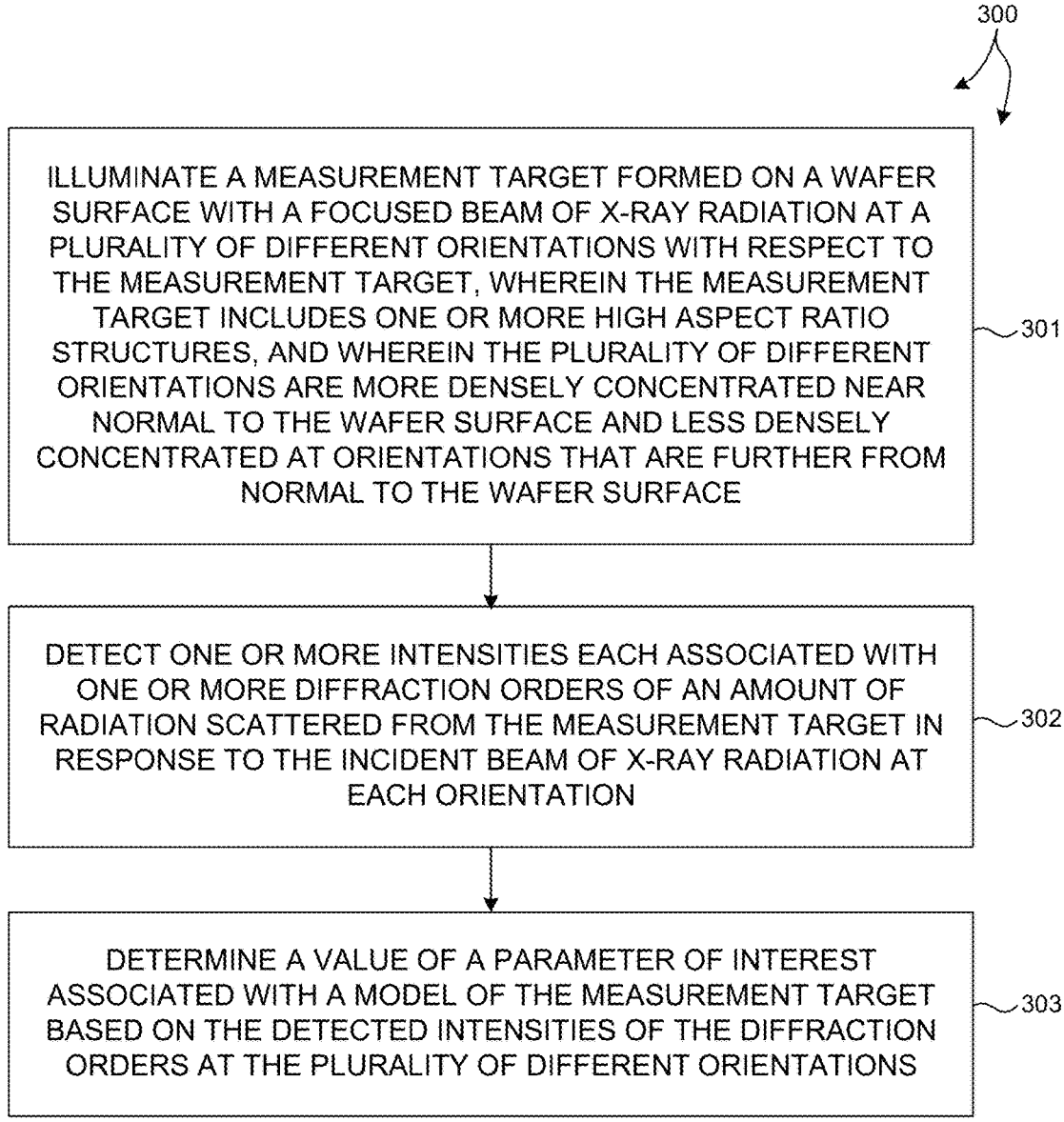
FIG. 9 depicts a flowchart illustrative of an exemplary method 300 of measuring high aspect ratio structures based on T-SAXS measurements.

FIG. 9 illustrates a method 300 suitable for implementation by the metrology systems 100 and 200 of the present invention. In one aspect, it is recognized that data processing blocks of method 300 may be carried out via a pre-programmed algorithm executed by one or more processors of computing system 130. While the following description is presented in the context of metrology systems 100 and 200, it is recognized herein that the particular structural aspects of metrology systems 100 and 200 do not represent limitations and should be interpreted as illustrative only.

In block 301, a measurement target formed on a wafer surface is illuminated with a focused beam of x-ray radiation at a plurality of different orientations with respect to the measurement target. The measurement target includes one or more high aspect ratio structures. In addition, the plurality of different orientations are more densely concentrated near normal to the wafer surface and less densely concentrated at orientations that are further from normal to the wafer surface.

In block 302, one or more intensities each associated with one or more diffraction orders of an amount of radiation scattered from the measurement target are detected in response to the incident beam of x-ray radiation at each orientation.

In block 303, a value of a parameter of interest associated with a model of the measurement target is determined based on the detected intensities of the diffraction orders at the plurality of orientations.

As described herein, the term "critical dimension" includes any critical dimension of a structure (e.g., bottom critical dimension, middle critical dimension, top critical dimension, sidewall angle, grating height, etc.), a critical dimension between any two or more structures (e.g., distance between two structures), and a displacement between two or more structures (e.g., overlay displacement between overlaying grating structures, etc.). Structures may include three dimensional structures, patterned structures, overlay structures, etc.

As described herein, the term "critical dimension application" or "critical dimension measurement application" includes any critical dimension measurement.

As described herein, the term "metrology system" includes any system employed at least in part to characterize a specimen in any aspect, including critical dimension applications and overlay metrology applications. However, such terms of art do not limit the scope of the term "metrology system" as described herein. In addition, the metrology systems described herein may be configured for measurement of patterned wafers and/or unpatterned wafers. The metrology system may be configured as a LED inspection tool, edge inspection tool, backside inspection tool, macro-inspection tool, or multi-mode inspection tool (involving data from one or more platforms simultaneously), and any other metrology or inspection tool that benefits from the measurement techniques described herein.

Various embodiments are described herein for a semiconductor processing system (e.g., an inspection system or a lithography system) that may be used for processing a specimen. The term "specimen" is used herein to refer to a wafer, a reticle, or any other sample that may be processed (e.g., printed or inspected for defects) by means known in the art.

As used herein, the term "wafer" generally refers to substrates formed of a semiconductor or non-semiconductor material. Examples include, but are not limited to, monocrystalline silicon, gallium arsenide, and indium phosphide. Such substrates may be commonly found and/or processed in semiconductor fabrication facilities. In some cases, a wafer may include only the substrate (i.e., bare wafer). Alternatively, a wafer may include one or more layers of different materials formed upon a substrate. One or more layers formed on a wafer may be "patterned" or "unpatterned." For example, a wafer may include a plurality of dies having repeatable pattern features.

A "reticle" may be a reticle at any stage of a reticle fabrication process, or a completed reticle that may or may not be released for use in a semiconductor fabrication facility. A reticle, or a "mask," is generally defined as a substantially transparent substrate having substantially opaque regions formed thereon and configured in a pattern. The substrate may include, for example, a glass material such as amorphous $SiO_2$. A reticle may be disposed above a resist-covered wafer during an exposure step of a lithography process such that the pattern on the reticle may be transferred to the resist.

One or more layers formed on a wafer may be patterned or unpatterned. For example, a wafer may include a plurality of dies, each having repeatable pattern features. Formation and processing of such layers of material may ultimately result in completed devices. Many different types of devices may be formed on a wafer, and the term wafer as used herein is intended to encompass a wafer on which any type of device known in the art is being fabricated.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, XRF disc, digital versatile disc (DVD), floppy disk and blu-ray disc where disks usually reproduce data magnetically, while discs reproduce data optically with lasers. Combinations of the above should also be included within the scope of computer-readable media.

Although certain specific embodiments are described above for instructional purposes, the teachings of this patent document have general applicability and are not limited to the specific embodiments described above. Accordingly, various modifications, adaptations, and combinations of various features of the described embodiments can be practiced without departing from the scope of the invention as set forth in the claims.

What is claimed is:

1. A metrology system comprising:
    an x-ray illumination source configured to generate an amount of x-ray radiation;
    an x-ray illumination optics subsystem configured to illuminate a measurement target formed on a wafer surface with a focused beam of the amount of x-ray radiation at a plurality of different orientations with respect to the measurement target, wherein the measurement target includes one or more structures, and wherein the plurality of different orientations are more densely concentrated near normal to the wafer surface and less densely concentrated at orientations that are further from normal to the wafer surface;
    an x-ray detector configured to detect one or more intensities each associated with one or more diffraction orders of an amount of radiation scattered from the measurement target in response to the incident beam of x-ray radiation at each orientation; and a computing system configured to
determine a value of a parameter of interest associated with a model of the measurement target based on the detected intensities of the diffraction orders at the plurality of different orientations.

2. The metrology system of claim 1, wherein the parameter of interest is a shape parameter.

3. The metrology system of claim 1, wherein the one or more structures has an overall depth of at least one micrometer.

4. The metrology system of claim 3, wherein the one or more structures is any of a spin transfer torque random access memory (STT-RAM), a three dimensional NAND memory (3D-NAND), a dynamic random access memory (DRAM), a three dimensional FLASH memory (3D-FLASH), resistive random access memory (Re-RAM), and a phase change random access memory (PC-RAM).

5. The metrology system of claim 1, wherein the one or more structures has an aspect ratio of at least twenty, wherein the aspect ratio is defined as a maximum height dimension divided by a maximum lateral extent dimension.

6. The metrology system of claim 1, wherein the one or more structures comprise alternating layers of different materials.

7. The metrology system of claim 1, wherein the x-ray illumination source includes any of a liquid metal jet x-ray illumination source, a solid anode x-ray illumination source, and an inverse Compton x-ray illumination source.

8. The metrology system of claim 1, wherein the measurement target is located within a scribe line area or within an active die area.

9. The metrology system of claim 1, wherein the determining the parameter of interest involves a fitting analysis of the detected intensities of the diffraction orders with a geometrically parameterized response model.

10. The metrology system of claim 9, wherein the computing system is further configured to determine a multi-dimensional image of the measurement target based on the detected intensities of the diffraction orders at the plurality of different orientations.

11. The metrology system of claim 10, wherein the computing system is further configured to modify the geometrically parameterized response model of the measurement target based on a difference between the image of the measurement target and the parameter of interest.

12. The metrology system of claim 1, wherein the determining of the value of the parameter of interest involves a combined fitting analysis of the detected intensities of the diffraction orders at the plurality of different orientations and detected optical intensities with a combined, geometrically parameterized response model, wherein the optical intensities are measured by an optical metrology tool.

13. A method comprising:
illuminating a measurement target formed on a wafer surface with a focused beam of x-ray radiation at a plurality of different orientations with respect to the measurement target, wherein the measurement target includes one or more structures, and wherein the plurality of different orientations are more densely concentrated near normal to the wafer surface and less densely concentrated at orientations that are further from normal to the wafer surface;
detecting one or more intensities each associated with one or more diffraction orders of an amount of radiation scattered from the measurement target in response to the incident beam of x-ray radiation at each orientation; and
determining a value of a parameter of interest associated with a model of the measurement target based on the detected intensities of the diffraction orders at the plurality of different orientations.

14. The method of claim 13, wherein the one or more structures has an overall depth of at least one micrometer.

15. The method of claim 13, wherein the one or more structures has an aspect ratio of at least twenty, wherein the aspect ratio is defined as a maximum height dimension divided by a maximum lateral extent dimension.

16. The method of claim 13, wherein the determining the parameter of interest involves a fitting analysis of the detected intensities of the diffraction orders with a geometrically parameterized response model.

17. The method of claim 16, further comprising:
determining a multi-dimensional image of the measurement target based on the detected intensities of the diffraction orders at the plurality of different orientations.

18. The method of claim 17, further comprising:
modifying the geometrically parameterized response model of the measurement target based on a difference between the image of the measurement target and the parameter of interest.

19. The method of claim 13, wherein the determining of the value of the parameter of interest involves a combined fitting analysis of the detected intensities of the diffraction orders at the plurality of different orientations and detected optical intensities with a combined, geometrically parameterized response model, wherein the optical intensities are measured by an optical metrology tool.

20. A metrology system comprising:
an x-ray illumination source configured to generate an amount of x-ray radiation;
an x-ray illumination optics subsystem configured to illuminate a measurement target formed on a wafer surface with a focused beam of the amount of x-ray radiation at a plurality of different orientations with respect to the measurement target, wherein the measurement target includes one or more structures, and wherein the plurality of different orientations are more densely concentrated near normal to the wafer surface and less densely concentrated at orientations that are further from normal to the wafer surface;
an x-ray detector configured to detect one or more intensities each associated with one or more diffraction orders of an amount of radiation scattered from the measurement target in response to the incident beam of x-ray radiation at each orientation; and
a non-transitory, computer-readable medium, comprising:
code for causing a computing system to determine a value of a parameter of interest associated with a model of the measurement target based on the detected intensities of the diffraction orders at the plurality of orientations.

21. The metrology system of claim 20, wherein the determining of the value of the parameter of interest involves a combined fitting analysis of the detected intensities of the diffraction orders at the plurality of different orientations and detected optical intensities with a combined, geometrically parameterized response model, wherein the optical intensities are measured by an optical metrology tool.

* * * * *